United States Patent [19]

Outtrup et al.

[11] Patent Number: 5,741,693
[45] Date of Patent: Apr. 21, 1998

[54] ALKALOPHILIC BACILLUS SP. AC13 AND PROTEASE, XYLANASE, CELLULASE OBTAINABLE THEREFROM

[75] Inventors: Helle Outtrup, Ballerup; Claus Dambmann, Søborg; Arne Agerlin Olsen, Virum; Henrik Bisgård-Frantzen, Lyngby; Martin Schülein, Copenhagen, all of Denmark

[73] Assignee: Novo Nordisk A/S, Bagsvaerd, Denmark

[21] Appl. No.: 343,600

[22] PCT Filed: Jul. 2, 1993

[86] PCT No.: PCT/DK93/00218

§ 371 Date: Nov. 30, 1994

§ 102(e) Date: Nov. 30, 1994

[87] PCT Pub. No.: WO94/01532

PCT Pub. Date: Jan. 20, 1994

[30] Foreign Application Priority Data

Jul. 2, 1992 [DK] Denmark ................. 870/92

[51] Int. Cl.⁶ ..................... C12N 9/50; C12N 9/54
[52] U.S. Cl. ............. 435/221; 435/219; 435/220; 435/252.5
[58] Field of Search .................. 435/221, 278, 435/832, 252.5, 187, 198, 201, 209, 189, 192, 219, 220; 252/174.12, DIG. 12

[56] References Cited

U.S. PATENT DOCUMENTS

| 3,676,352 | 7/1972 | Grimm et al. | 435/187 |
|---|---|---|---|
| 3,687,853 | 8/1972 | Natali et al. | 252/89 |
| 3,723,327 | 3/1973 | Van Kampen et al. | 252/110 |
| 3,749,671 | 7/1973 | Gedge III | 435/187 |
| 4,480,037 | 10/1984 | Ichishima et al. | 435/221 |
| 4,764,470 | 8/1988 | Durham et al. | 435/221 |
| 4,771,003 | 9/1988 | Stellwag et al. | 435/221 |

FOREIGN PATENT DOCUMENTS

| 232169 | 8/1987 | European Pat. Off. |
|---|---|---|
| 0 270 974 | 6/1988 | European Pat. Off. |
| 0 339 550 | 11/1989 | European Pat. Off. |
| 0 468 464 | 1/1992 | European Pat. Off. |
| 3328619 | 2/1985 | Germany |
| 4219104 | 12/1993 | Germany |
| 63101494 | 5/1988 | Japan |
| 1101884 | 4/1989 | Japan |
| 5252949 | 10/1993 | Japan |
| WO 91/10732 | 7/1991 | WIPO |
| WO 91/18978 | 12/1991 | WIPO |
| WO 92/03540 | 3/1992 | WIPO |
| WO 92/17576 | 10/1992 | WIPO |
| WO 92/17577 | 10/1992 | WIPO |
| WO 92/17578 | 10/1992 | WIPO |

OTHER PUBLICATIONS

Abstract of Japanese Patent Appln. No. 1-91772.
Abstract of Japanese Patent Appln. No. 1-112982.

*Primary Examiner*—Leon B. Lankford, Jr.
*Attorney, Agent, or Firm*—Steve T. Zelson, Esq.; Elias J. Lambiris, Esq.

[57] ABSTRACT

The present invention relates to proteases obtained from a strain of Bacillus sp. AC13, and having (a) an apparent molecular weight of approximately 30 kD as determined by SDS-PAGE; (b) an isoelectric point of approximately 9.3 as determined by isoelectric focusing on LKB Ampholine PAG plates; (c) a pH optimum above 10 determined at 25° C. with casein as substrate; (d) a temperature optimum in the range of 45°–55° C. determined at pH 9.5 with casein as substrate; and (e) immunochemical properties identical or partially identical to those of a protease derived from Bacillus sp. AC13, NCIMB No. 40482.

8 Claims, 2 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Bacillus sp.
        (B) STRAIN: AC 13 NCIMB 40482

(xi) SEQUENCE DESCRIPTION: SEQ ID NO:1:

```
Asp Xaa Asp Xaa Val Val Glu Glu His Gly Gln Leu Arg Ile Xaa Asn
 1           5                   10                  15
Gly Xaa Leu
```

ALKALOPHILIC BACILLUS SP. AC13 AND PROTEASE, XYLANASE, CELLULASE OBTAINABLE THEREFROM

CROSS-REFERENCE TO RELATED APPLICATIONS

This application is a continuation of PCT/DK93/00218 filed Jul. 2, 1993, published as WO94/01532 Jan. 20, 1994, which is incorporated herein by reference.

TECHNICAL FIELD

The present invention relates to novel microorganisms, novel enzymes obtainable herefrom, and to a method of producing the novel enzymes. More specifically, the invention relates to novel enzymes obtainable from strains of the novel alkalophilic species Bacillus sp. AC13.

Moreover, the invention relates to a method for producing the enzymes of the invention, and to the use of the enzymes, particularly in detergents or in the paper pulp industry.

SUMMARY OF THE INVENTION

It is an object of the present invention to provide novel microorganisms capable of expressing valuable novel enzymes for industrial applications, as well as novel enzymes of different kinds obtainable from these organisms.

Accordingly, the invention provides isolated biologically pure cultures of strains of the alkalophilic species Bacillus sp. AC13.

In another aspect, the invention provides enzymes obtainable from strains of Bacillus sp. AC13, and having immunochemical properties identical or partially identical to those of an enzyme derived from Bacillus sp. AC13, NCIMB No. 40482.

In a more specific aspect, the invention provides proteases obtainable from strains of Bacillus sp. AC13, and having immunochemical properties identical or partially identical to those of a protease derived from Bacillus sp. AC13, NCIMB No. 40482.

In another specific aspect, the invention provides xylanases obtainable from strains of Bacillus sp. AC13, and having immunochemical properties identical or partially identical to those of a xylanase derived from Bacillus sp. AC13, NCIMB No. 40482.

In a third specific aspect, the invention provides cellulases obtainable from strains of Bacillus sp. AC13, and having immunochemical properties identical or partially identical to those of a cellulase derived from Bacillus sp. AC13, NCIMB No. 40482.

In a third aspect, the invention provides a process for the preparation of an enzyme of the invention, the process comprising cultivation of a strain of Bacillus sp. AC13, preferably the strain Bacillus sp. AC13, NCIMB No. 40482, or a mutant or a variant thereof, in a suitable nutrient medium, containing carbon and nitrogen sources and inorganic salts, followed by recovery of the desired enzyme.

In further aspects, the invention provides detergent additives and detergent compositions comprising an enzyme of the invention.

Moreover, the invention relates to the use of a xylanase of the invention in processes for treatment of lignocellulosic pulp.

BRIEF DESCRIPTION OF DRAWINGS

The present invention is further illustrated by reference to the accompanying drawings, in which.

DETAILED DISCLOSURE OF THE INVENTION

The Microorganism

Figure 1:
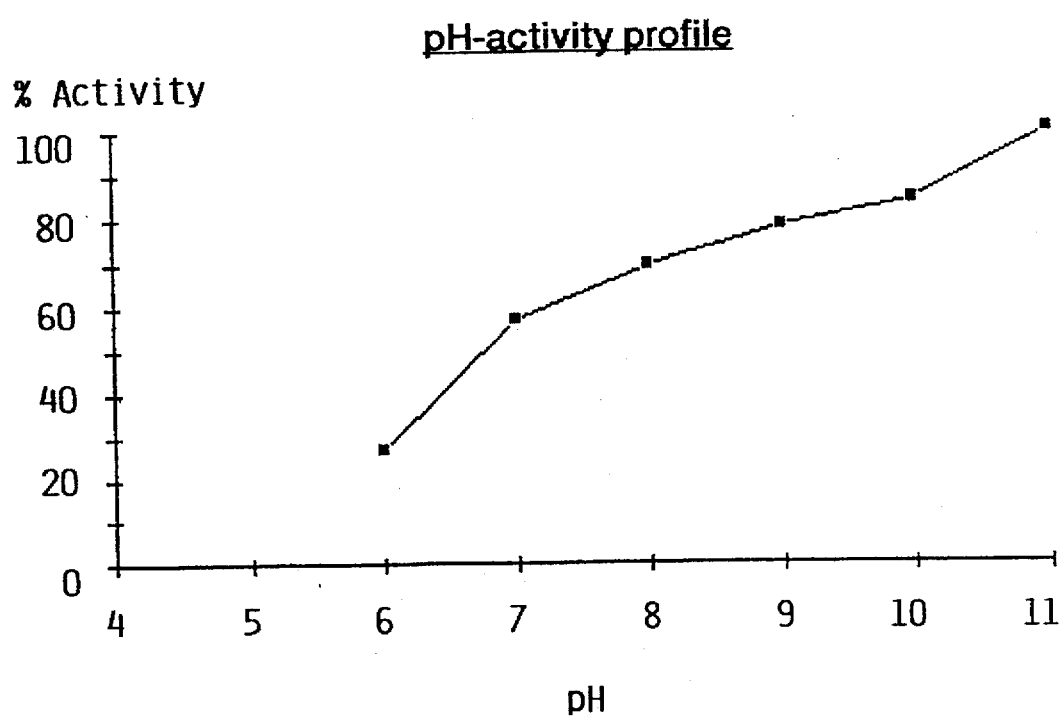
FIG. 1 shows the relative activity (% rel.) of a protease of the invention at various pH, determined at 25° C. with casein as substrate.

The present invention relates to microorganisms of the novel alkalophilic species Bacillus sp. AC13, represented by the type culture Bacillus sp. AC13, NCIMB 40482.

The strain Bacillus sp. AC13, NCIMB 40482, has been deposited on 3 Mar. 1992 according to the Budapest Treaty on the International Recognition of the Deposits of Microorganisms for the Purpose of Patent Procedures, at National Collections of Industrial and Marine Bacteria Ltd., 23 St. Machar Drive, Aberdeen AB2 1RY, Scotland, UK, under Accession No. NCIMB 40482.

The microorganisms of this invention are aerobic, rod shaped, spore forming bacteria, and therefore belonging to the genus Bacillus.

Morphologically they can be described as rods having a diameter of 0.6–0.9 μm and a length of 4–8 μm. The spores are ellipsoid to round, approximately 1.2×0.8 μm, terminal swelling the sporangia, giving the sporangium a characteristic racket or drumstick like shape.

The microorganisms of Bacillus sp. AC13 are obligately alkalophilic, requiring carbonate buffer pH 9 to 10 in the agar media for growth. Optimal growth is observed at 37° C., at pH 9.5–10. No growth at 50° C. and no growth at pH 7.

Colonies on potato dextrose agar (Difco™) added 0.1M sodium sesquicarbonate are white with characteristic dendroid to hairy edges.

The microorganisms can be further described by the following characteristics.

| | | |
|---|---|---|
| NaCl tolerance<br>weak growth at 12% | 0–10% | |
| Growth temperature<br>no growth at 50° C. | ≦45° C. | |
| Hydrolysis of | casein | positive |
| | gelatine | positive |
| | pullulan | negative |
| | starch | positive |
| | cellulose | positive |
| | xylan | positive |
| Catalase reaction | positive | |
| Aminopeptidase test | negative | |
| Deamination of phenylalanine | negative | |
| Reduction of nitrate | positive | |
| Major fatty acids | C 15:0 ISO (≈45%) | |
| | C 15:0 ANTEISO (≈25%) | |
| | ISO 17:1 w10c (≈10%) | |
| | Unsaturated: 20% | |
| | Branched approx. 50% | |

Cultivation of the Microorganism

The microorganism of the invention can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes involving the cultivation of bacteria. Illustrative examples are soybean meal, cotton seed meal, peanut meal, casein, corn, corn steep liquor, yeast extract, urea and albumin. In addition, the nutrient medium should also contain usual trace substances.

Since the novel Bacillus species of this invention are alkalophilic and unable to grow at pH below 7, the cultivation is preferably conducted at alkaline pH values, which can be obtained by addition of suitable buffers such as sodium carbonate or mixtures of sodium carbonate and sodium bicarbonate, after sterilization of the growth medium. For cultivation in tank fermentors it is necessary to use artificial aeration. The rate of aeration is similar to that used in conventional tank fermentation.

After fermentation, liquid enzyme concentrates may be produced by removal of coarse material from the broth or, if desired, concentration of the broth by evaporation at low temperature or by reverse osmosis. Finally, preservatives may be added to the concentrate.

Solid enzyme preparations may be prepared from the purified and/or concentrated broth by precipitation with salts, such as $Na_2SO_4$ or water-miscible solvents, such as ethanol or acetone. Removal of the water in the broth by suitable drying methods such as spray-drying may also be employed.

The microorganisms of the invention have been found to be able to produce valuable novel enzymes, in particular proteases, xylanases and cellulases.

The Enzymes

The enzymes of the invention are obtainable by cultivation of a microorganism of the invention, preferably Bacillus sp. AC13, NCIMB No. 40482, or a mutant or a variant thereof, in a suitable nutrient medium, containing carbon and nitrogen sources and inorganic salts. The enzymes may also be obtained by recombinant DNA-technology.

In more specific aspects, the enzymes of the present invention can be further described by the following physical-chemical characteristics.

The Proteases

In a specific embodiment of the invention, a protease can be further characterized by having an apparent molecular weight of approximately 30 kD as determined by SDS-PAGE, and a pI of approximately 9.3 as determined by isoelectric focusing on LKB Ampholine PAG plates.

The protease can also be characterized by having proteolytic activity at pH values of from below pH 6 to above pH 11, having optimum above pH 10, around pH 11, when determined at 25° C. with casein as substrate.

Moreover, the protease can be characterized by having proteolytic activity at temperatures of from approximately 15° C. to above 70° C., having activity optimum at temperatures in the range 45°–55° C., around 50° C., when determined at pH 9.5 with casein as substrate. This activity optimum can be detected with or without sodium tripolyphosphate, which is a common ingredient in many commercial detergents.

The Xylanases

In a specific embodiment of the invention, a xylanase can be further characterized by having an apparent molecular weight of approximately 25 kD when determined by SDS-PAGE, and a pI of approximately 9 when determined by isoelectric focusing on LKB Ampholine PAG plates.

The Cellulases

In a specific embodiment of the invention, two cellulases can be further characterized, one by having an apparent molecular weight of approximately 45 kD when determined by SDS-PAGE, and a pI of approximately 4.3 when determined by isoelectric focusing on LKB Ampholine PAG plates, and one by having an apparent molecular weight of approximately 55 kD when determined by SDS-PAGE, and a pI of approximately 4.5 when determined by isoelectric focusing on LKB Ampholine PAG plates.

Immunochemical Properties

The enzymes of the invention have immunochemical properties identical or partially identical (i.e. at least partially identical) to those of an enzyme derived from the strain Bacillus sp. AC13, NCIMB No. 40482.

The immunochemical properties can be determined immunologically by cross-reaction identity tests. The identity tests can be performed by the well-known Ouchterlony double immunodiffusion procedure or by tandem crossed immunoelectrophoresis according to Axelsen N. H.; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

Monospecific antisera are generated according to the above mentioned method by immunizing rabbits with the purified enzymes of the invention. The immunogens are mixed with Freund's adjuvant and injected subcutaneously into rabbits every second week. Antisera are obtained after a total immunization period of 8 weeks, and immunoglobulins are prepared therefrom as described by Axelsen N. H., supra.

Assay for Proteolytic Activity

The proteolytic activity is determined with casein as substrate.

One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5.

A folder AF 228/1 describing the analytical method is available upon request to Novo Nordisk A/S, Denmark, which folder is hereby included by reference.

Assay for Xylanolytic Activity

The xylanolytic activity is measured in endo-xylanase units (EXU), determined at pH 9.0 with remazol-xylan as substrate.

A xylanase sample is incubated with remazol-xylan substrate. The background of non-degraded dyed substrate is precipitated by ethanol. The remaining blue colour in the supernatant is proportional to the xylanase activity, and the xylanase units are then determined relatively to an enzyme standard at standard reaction conditions, i.e. at 50.0°±0.1° C., pH 9.0, and 30 minutes' reaction time.

A folder AF 293.9/1 describing the analytical method is available upon request to Novo Nordisk A/S, Denmark, which folder is hereby included by reference.

Assay for Cellulytic Activity

The cellulytic activity is measured in cellulase viscosity units (CEVU), determined at pH 9.0 with carboxymethyl cellulose (CMC) as substrate.

Cellulase viscosity units are determined relatively to an enzyme standard (<1% water, kept in $N_2$ atmosphere at –20° C.; arch standard at –80° C.). The standard used, 17–1187, is 4400 CEVU/g under standard incubation conditions, i.e. pH 9.0, Tris Buffer 0.1M, CMC 7 LFD substrate 33.3 g/l, 40.0° C. for 30 minutes.

A folder AF 253/1 describing the analytical method is available upon request to Novo Nordisk A/S, Denmark, which folder is hereby included by reference.

Industrial Applications

The enzymes of this invention possess valuable properties allowing for various industrial applications. In particular the proteases and cellulases of the invention, in being alkaline, find potential application in e.g. detergent compositions. The cellulases may find potential application in the textile industry, e.g. for Bio-Polishing. The xylanases may find application in e.g. the paper pulp industry.

The following examples further illustrate the present invention, and they are not intended to be in any way limiting to the scope of the invention as claimed.

EXAMPLE 1

Cultivation Example

The strain Bacillus sp. AC13, NCIMB 40482, was cultivated at 30° C. on a rotary shaking table (300 r.p.m.) in 500 ml baffled Erlenmeyer flasks containing 100 ml of medium of the following composition (per liter):

| | |
|---|---|
| Potato starch | 100 g |
| Ground barley | 50 g |
| Soybean flour | 20 g |
| $Na_2HPO_4 \times 12\ H_2O$ | 9 g |
| Pluronic ® | 0.1 g |
| Sodium caseinate | 10 g |

The starch in the medium is liquified with α-amylase and the medium is sterilized by heating at 120° C. for 45 minutes.

After sterilization the pH of the medium is adjusted to 9.7 by addition of 10 ml 1M sodium sesquicarbonate to each flask.

After 3 days of incubation the following activities were observed:

| | |
|---|---|
| Proteolytic activity | 20 CPU/l |
| Xylanolytic activity | 10 EXU/g |
| Cellulytic activity | 4 CEVU/g |

Isoelectric focusing on gels overlayered with different substrates at least 2 different proteases, at least 4 different xylanases, and at least 2 different cellulases were detected.

The major proteolytic band has a pI of approximately 9.3 and a molecular weight of approximately 30 kD.

The major xylanolytic band has a pI of approximately 9 and a molecular weight of approximately 25 kD.

The major cellulytic band has a pI of approximately 4.3 and a molecular weight of approximately 45 kD.

EXAMPLE 2

Purification of the Proteolytic Compounds

After cultivation, the proteolytic activity of the fermentation broth of Ex. 1 was found to be 20 CPU/l. In this fermentation broth at least two proteolytic enzymes have been identified by isoelectric focusing on LKB Ampholine PAG plates.

After separation of the solid material, the major proteolytic component was purified by a conventional chromatographic method. From 1 liter of culture broth yield was 50 ml of protease preparation with a proteolytic activity of 236 CPU/l (60%).

The purified protease has an apparent pI value of 9.3 when determined by isoelectric focusing on LKB Ampholine PAG plates. By SDS-PAGE the apparent molecular weight of the protease is found to be 30 kD. Purity was more than 90% as judged by both SDS-PAGE and isoelectric focusing.

Figure 2:
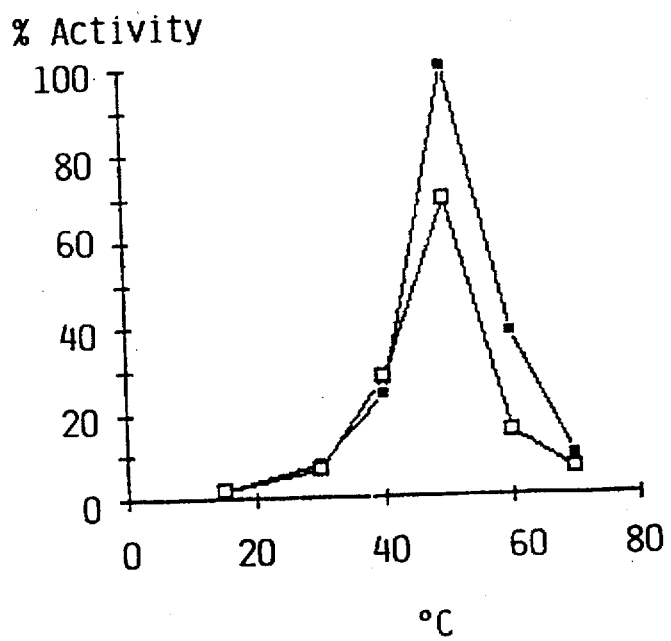
FIG. 2 shows the relative activity (% rel.) of a protease of the invention at various temperatures (■Buffer pH 9.5; □ Buffer pH 9.5 containing 0.1% STPP), determined at pH 9.5 with casein as substrate.

The activity was determined using the assay for proteolytic activity described above. The results of these experiments are presented on the appended FIGS. 1–2.

EXAMPLE 3

Purification of the Xylanolytic Compounds

In the fermentation broth, as obtained according to Ex. 1, at least four xylanolytic enzymes have been identified by isoelectric focusing combined with an overlayer of xylan. The xylanolytic enzymes cover the pI range of from 5 to 9.5.

From the fermentation broth of Ex. 1, a xylanase with an alkaline pI (the major xylanolytic component) was purified to homogeneity by conventional chromatographic techniques involving cation exchange chromatography on S-Sepharose High Load™ and Mono S™, hydrophobic adsorption chromatography on Phenyl-Sepharose, as well as affinity chromatography to specific removal of proteinases.

The purified xylanase has an apparent pI value of 9 in a 3.5 to 9.5 isoelectric focusing gel. By SDS-PAGE the apparent molecular weight of the xylanase is found to be 25 kD.

EXAMPLE 4

Purification of the Cellulytic Compounds

In the fermentation broth obtained according to Ex. 1 at least two cellulytic enzymes have been identified by isoelectric focusing.

The fermentation broth of Ex. 1 was filtrated and applied on a cellulase affinity column. After wash at pH 8.5 in Tris buffer, the column was eluted at high pH 11.8 with triethylamine. The pH in the eluate was adjusted to 7.5 and UF-concentrated and washed out with Tris buffer.

The concentrate was applied on a Mono Q™ column (Pharmacia) and eluted with a linear gradient with 15 column volumes in Tris buffer pH 9.0 with 0.5M NaCl.

The cellulase containing fractions were subjected to isoelectric focusing and SDS-PAGE, and two cellulytic components were found, one having a MW of approx. 45 kD and a pI of approx. 4.3, and one having a MW of approx. 55 kD and a pI of approx. 4.5.

EXAMPLE 5

N-Terminal Amino-Acid Analysis

The N-terminal amino-acid sequence of the cellulase, having a MW of approx. 45 kD, obtained according to Ex. 4, was determined using standard methods for obtaining and sequencing peptides [Findlay & Geisow (Eds.), Protein sequencing—a practical approach, 1989, IRL Press].

The N-terminal amino-acid sequence was found to be (SEQ ID No. 1 of the attached sequence listing):

Asp-Xaa-Asp-Xaa-Val-Val-Glu-Glu-His-Gly-Gln-Leu-Arg-Ile-Xaa-Asn-Gly-Xaa-Leu.

We claim:

1. An isolated protease obtained from a strain of Bacillus sp. AC13, and having (a) an apparent molecular weight of approximately 30 kD as determined by SDS-PAGE;

(b) an isoelectric point of approximately 9.3 as determined by isoelectric focusing on LKB Ampholine PAG plates;

(c) a pH optimum above 10 determined at 25° C. with casein as substrate;

(d) a temperature optimum in the range of 45°–55° C. determined at pH 9.5 with casein as substrate; and (e) immunochemical properties identical or partially identical to those of a protease derived from Bacillus sp. AC13, NCIMB No. 40482.

2. The protease according to claim 1, wherein the pH optimum is around 50° C.

3. The protease according to claim 1, wherein the strain is NCIMB No. 40482 or a mutant thereof.

4. A process for preparing a protease according to claim 1, comprising (a) cultivating a strain of Bacillus sp. AC13 or a mutant thereof, in a suitable nutrient medium containing carbon and nitrogen sources and inorganic salts; and (b) recovering the protease.

5. The process according to claim 4, wherein the strain is NCIMB No. 40482 or a mutant thereof.

6. A detergent additive comprising a protease according to claim 1 in the form of a granulate, a liquid, a slurry, or a protected enzyme.

7. A detergent composition comprising a protease according to claim 1 and a surfactant.

8. The detergent composition according to claim 7, further comprising one or more other enzymes selected from the group consisting of lipases, amylases, cellulases, oxidases and peroxidases.

\* \* \* \* \*

UNITED STATES PATENT AND TRADEMARK OFFICE
CERTIFICATE OF CORRECTION

PATENT NO. : 5,741,693
DATED : April 21, 1998
INVENTOR(S) : Outtrup et al.

Page 1 of 1

It is certified that error appears in the above-identified patent and that said Letters Patent is hereby corrected as shown below:

<u>Column 7, claims,</u>
Line 44, please delete "pH", and insert -- temperature --

Signed and Sealed this

Twenty-eighth Day of August, 2001

Attest:

*Nicholas P. Godici*

*Attesting Officer*

NICHOLAS P. GODICI
*Acting Director of the United States Patent and Trademark Office*